(12) United States Patent
Hellenbrand et al.

(10) Patent No.: US 10,559,021 B2
(45) Date of Patent: Feb. 11, 2020

(54) METHOD FOR OPERATING A PHARMACY ORDER-PICKING SYSTEM

(71) Applicant: CareFusion Germany 326 GmbH, Kelberg (DE)

(72) Inventors: Christoph Hellenbrand, Kaifenheim (DE); Andreas Klapperich, Rieden (DE); Andreas Bause, Kruft (DE); Dennis Reif, Kaisersesch (DE)

(73) Assignee: CAREFUSION GERMANY 326 GMBH, Kelberg (DE)

( * ) Notice: Subject to any disclaimer, the term of this patent is extended or adjusted under 35 U.S.C. 154(b) by 1207 days.

(21) Appl. No.: 14/382,308

(22) PCT Filed: Feb. 6, 2013

(86) PCT No.: PCT/EP2013/052286
§ 371 (c)(1),
(2) Date: Aug. 29, 2014

(87) PCT Pub. No.: WO2013/127607
PCT Pub. Date: Sep. 6, 2013

(65) Prior Publication Data
US 2015/0032568 A1    Jan. 29, 2015

(30) Foreign Application Priority Data

Feb. 29, 2012   (EP) ................................... 12157483

(51) Int. Cl.
*G06Q 30/00* (2012.01)
*G06Q 30/06* (2012.01)
(Continued)

(52) U.S. Cl.
CPC ..... *G06Q 30/0633* (2013.01); *G06Q 10/0836* (2013.01); *G06Q 50/22* (2013.01)

(58) Field of Classification Search
CPC . G06Q 30/0633; G06Q 10/0836; G06Q 50/22
(Continued)

(56) References Cited

U.S. PATENT DOCUMENTS

| 3,504,245 A | 3/1970 | Cotton et al. |
| 4,415,975 A | 11/1983 | Burt |
| 2008/0044262 A1* | 2/2008 | Kim ..................... B65G 1/0421 414/273 |

FOREIGN PATENT DOCUMENTS

| CH | 520612 A | 3/1972 |
| CN | 101125603 A | 2/2008 |
| (Continued) |

OTHER PUBLICATIONS

Jordt, Andreas (2009). Automatic High-Precision Self-Calibration of Camera-Robot Systems. 2009 IEEE International Conference on Robotics and Automation. May 12-17, 2009. https://ieeexplore.ieee.org/stamp/stamp.jsp?tp=&arnumber=5152570 (Year: 2009).*

(Continued)

*Primary Examiner* — Jason B Dunham
*Assistant Examiner* — Anand R Loharikar
(74) *Attorney, Agent, or Firm* — Morgan, Lewis & Bockius LLP

(57) ABSTRACT

The present disclosure relates to a method for operating a pharmacy order-picking device. The present method reduces the susceptibility of the pharmacy order-picking device to disruption. To detect a positioning deviation of the control appliance in the horizontal direction, at least one desired value of at least one reference position is made available, the control appliance is brought to a position corresponding to the desired value in the horizontal direction and, when a signal characteristic of a reference position is detected, an actual value of this reference position is determined. A desired value is compared with a corresponding actual value, or two actual values are compared with each other, and a deviation is determined. If a deviation is determined that exceeds a limit value, a signal pointing to the need for (Continued)

a correction is output. Depending on the deviation, automatic correction of the position deviation can be performed.

9 Claims, 6 Drawing Sheets

(51) Int. Cl.
*G06Q 10/08* (2012.01)
*G06Q 50/22* (2018.01)

(58) Field of Classification Search
USPC .............................................. 705/26.1–27.2
See application file for complete search history.

(56) References Cited

FOREIGN PATENT DOCUMENTS

| CN | 101529980 | A  | 9/2009 |
|----|-----------|----|--------|
| EP | 1035044   | A2 | 9/2000 |
| FR | 2608567   | A1 | 6/1988 |
| GB | 2200477   | A  | 8/1988 |
| JP | S60183405 | A  | 9/1985 |
| JP | S6160504  | A  | 3/1986 |

OTHER PUBLICATIONS

Chinese Office Action for Application No. 201380009780.X, dated Aug. 4, 2015, 19 pages.
Extended European Search Report for Application No. 12157483.4, dated Jul. 20, 2013, 19 pages.
International Preliminary Report on Patentability for Application No. PCT/EP2013/052286, date unknown, 6 pages.
International Search Report for Application No. PCT/EP2013/052286, dated Feb. 22, 2013, 3 pages.

* cited by examiner

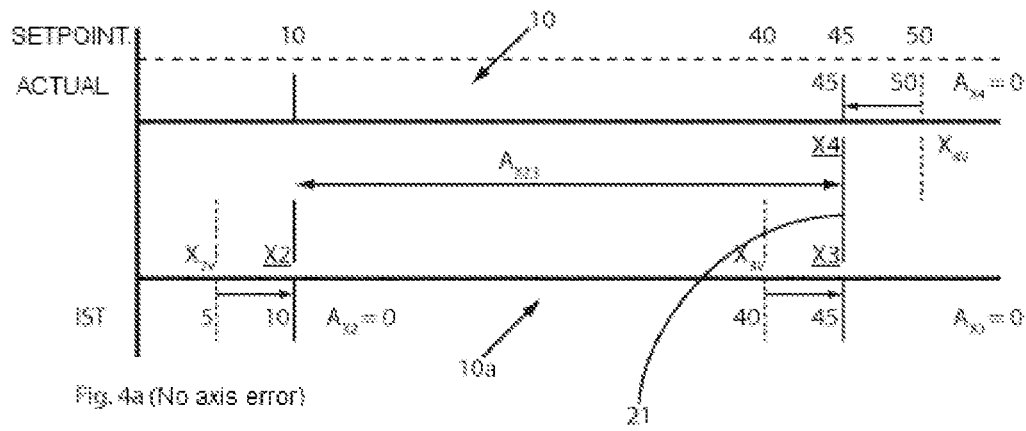
Fig. 4a (No axis error)
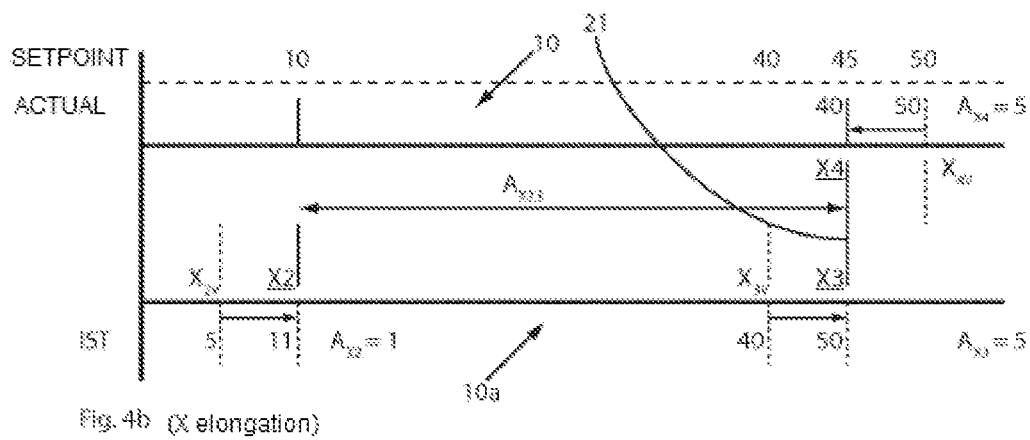
Fig. 4b (X elongation)
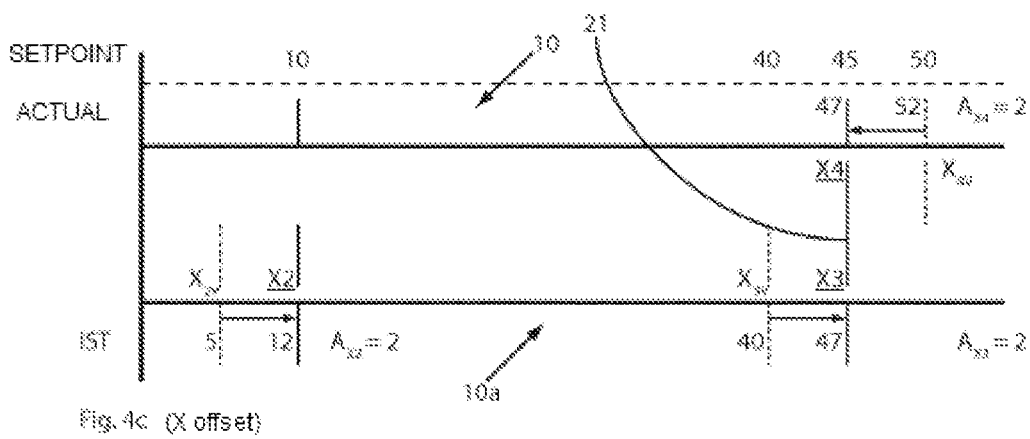
Fig. 4c (X offset)

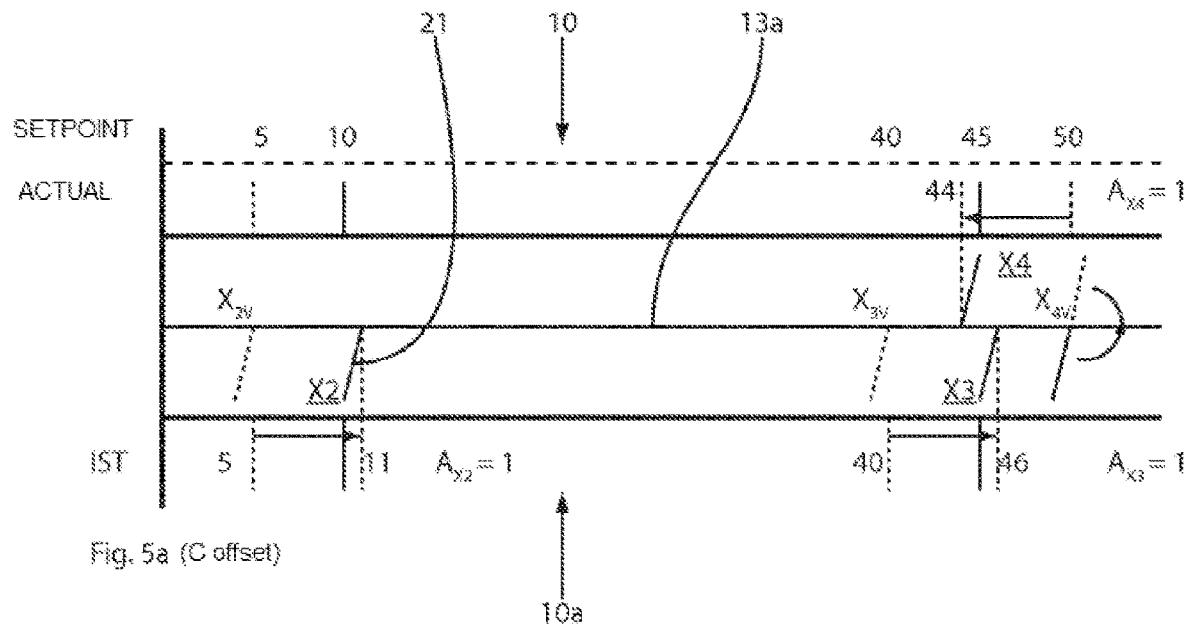
Fig. 5a (C offset)
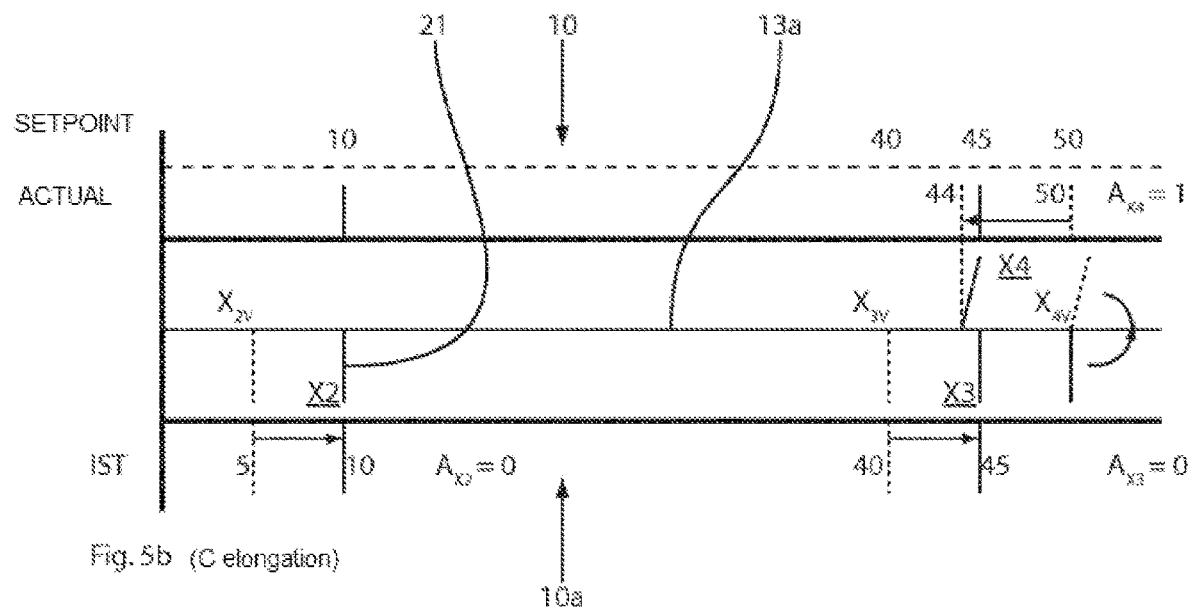
Fig. 5b (C elongation)

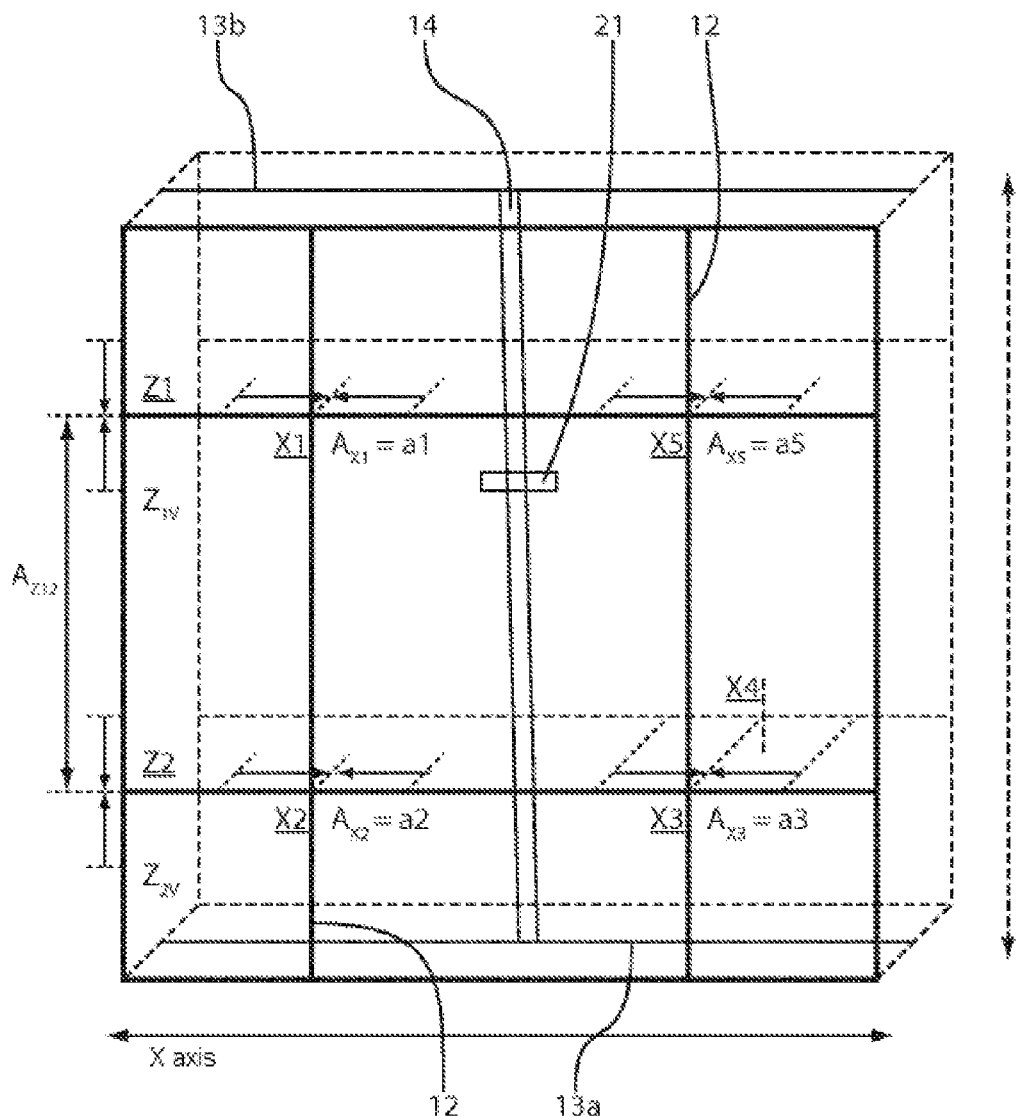
Fig. 6 (Z inclined position)

METHOD FOR OPERATING A PHARMACY ORDER-PICKING SYSTEM

CROSS-REFERENCE TO RELATED APPLICATION

This application is the U.S. National Phase under 35 U.S.C. § 371 of International Application No. PCT/EP2013/052286, filed on Feb. 6, 2013, which claims the benefit of EP 12157483.4, filed Feb. 29, 2012. The entire contents of these applications are incorporated by reference herein.

BACKGROUND

In some pharmacy order-picking systems, a large number of different drug packages of various sizes (piece goods) may be stored on elongated shelves in a chaotic fashion that is optimized as to space. Some pharmacy-order picking systems place drug packages on the shelves and/or retrieve them from the shelves with the help of an operating unit, wherein the operating unit has a gripping device for gripping the drug packages. For placing the drug packages on a shelf, the drug packages are identified, measured (e.g., the measurements are determined in three dimensions) and conveyed into a gripping area of the gripping device of a shelf operating system (see DE 195 09 951 C2, for example).

SUMMARY

The present disclosure relates to a method for operating a pharmacy order-picking system with at least one shelf unit, each shelf unit having a plurality of shelves extending in a horizontal direction (X axis) and a plurality of shelf walls extending in a vertical direction (Z axis), at least one operating device being movable horizontally and vertically in front of the row of shelves and having a gripping device for placing drug packages on the shelves and/or retrieving them from the shelves, wherein the operating unit has at least one sensor and has a control unit connected to the operating unit.

Based on the measurements of the drug packages to be stored as well as the occupancy of the pharmacy order-picking system, optimal storage sites for the drug packages are calculated and stored in the control unit. To calculate an optimal storage site, it may also be necessary for the control unit to know the precise geometric structure of the pharmacy order-picking systems, and in particular, the location and/or arrangement and dimensions of the shelves and walls. In this way is it possible, for example, to prevent a position that is occupied by a wall from being selected within the pharmacy order-picking system. The location of a drug package is calculated as space coordinates (with an X, Y, Z axis component) within the pharmacy order-picking system. The reference point (origin) for these space coordinates may be, for example, a certain reference point within the device (for example, certain position of the operating unit/gripping device). Each shelving compartment may be formed by shelves and dividers to have its own reference point. The position (and/or the space coordinates) of a drug package is/are then determined within the shelving compartment just as uniquely based on the space coordinates of the reference point of the compartment and the space coordinate of the drug package within the shelving compartment.

For further storage, the gripping device grips the drug packages in the gripping area and conveys them to the predetermined storage site. For optimal utilization of space, the shelves are occupied densely but drug packages of different dimensions and different types may be stored side by side.

If a certain drug package is to be retrieved from storage—for example, because of a request by a customer of the pharmacy—the operating unit selects the storage site of the desired drug package, grips the drug package with the griping device, and transfers it to a discharge point and/or to a conveyance mechanism, which conveys the drug package to a discharge point (for example, in the sales room of a pharmacy). Conveyance might not be necessary, depending on the structural situation.

The accuracy of the positioning of the operating unit and/or the gripping device in storage/retrieval from storage is desired for smooth operation of the pharmacy order-picking system. When placing an item on the shelf, for example, the control unit calculates a storage location with certain space coordinates on the basis of the geometry of the pharmacy order-picking system, the dimensions of the drug package to be placed on the shelf and the occupancy of the system. This storage site is to be approached by the operating unit, and the drug package is to be placed on a shelf at the calculated storage site. Inaccurate positioning of the operating unit may prevent fault-free placement on the shelf (for example, if a position that includes a shelving wall is approached or if the shelving position thus approached is already occupied). Based on retrieval from storage, inaccurate positioning of the operating unit and the gripping device means that it may be impossible under some circumstances to retrieve a certain drug package from storage using the operating unit, and in some situations it may be necessary to retrieve a drug package by hand, which thus leads to unwanted delays and a disturbance in automatic operation.

The operating unit itself is a complex mechanical device having a plurality of drive mechanisms, which make it possible for the operating unit and the gripping device to move in both horizontal and vertical directions (X and Z axes). During operation of the pharmacy order-picking system, the operating unit and the gripping device are exposed to high loads, which may result in a creeping loss of accuracy with which the operating unit can be positioned with respect to a given location within the system.

If the drive mechanism for positioning in X direction, for example, includes one or more toothed belts, these belts may become stretched out over time. That is, the toothed belt undergoes a change in length. If the stretched toothed belt is then driven by a corresponding motor (for example, a stepping motor) to the storage site by the same number of steps that would be necessary for positioning if the toothed belt were not stretched out, this would result in a mistake in the positioning in X direction (the actual position may not be reached because of the stretched length of the toothed belt). Depending on the precise design of the drive mechanisms, additional problems may also prevent accurate positioning. Inaccurate positioning of the operating unit thus causes a disturbance in automatic (continuous) operation of a pharmacy order-picking system because there is the risk that the drug packages cannot be placed on the shelf and retrieved with the operating unit.

The object of the present disclosure is therefore to provide a method for operating a pharmacy order-picking system which will prevent susceptibility to disturbances in automatic operation of the pharmacy order-picking system.

The pharmacy order-picking system, which is operated according to the disclosure includes at least one shelf unit, each having a plurality of shelves extending in a horizontal direction and a plurality of shelving walls extending in a vertical direction, at least one operating unit that can be moved horizontally and vertically in front of the shelving, having a gripping device for placing drug packages on the shelf and/or retrieving them from the shelf, such that the operating unit has at least one sensor and a control unit, which is connected to the operating unit controls all of the operating sequences within the pharmacy order-picking system.

For operation of a pharmacy order-picking system in a method described herein for operating a pharmacy order-picking system, at least one setpoint value of at least one reference position is made available for detection of a deviation in positioning of the operating unit in the horizontal direction (X axis).

A reference position with regard to the X axis may be the position of a certain shelving wall within the pharmacy order-picking system, for example. The setpoint value then characterizes the distance of the reference position from a reference point within the pharmacy order-picking system. If two setpoint values of two reference positions are supplied, then the reference positions can correspond to the arrangements of two shelving walls within the pharmacy order-picking system. Other points may also be selected as reference positions. It is important that these positions do not undergo any spatial change in the course of operation.

Due to the type of installed drive mechanism for the movement of the operating unit in X direction as well as its characteristics, the control unit knows how to approach (for example, with X motor steps when using a stepping motor) a reference position with a predefined precision in a "faultless" drive mechanism (e.g., having "origin characteristics").

In a method described herein, a position corresponding to a setpoint value is approached by the operating units in the horizontal direction, wherein the aforementioned position deviates from the setpoint value of the reference position. That is, the position being approached is behind or in front of the actual reference position.

With the sensor turned on (the sensor may not be turned on until reaching the position corresponding to the setpoint value or it is in a continuous operating state), the operating unit is advanced further in the horizontal direction toward the actual setpoint value, and an actual value of this reference position is determined when a signal that is characteristic of the reference position is detected by the sensor. The sensor may be an optical sensor according to the triangulation principle, for example, which can determine the distance of the sensor from an object by which the sensor passes. The actual value that is determined indicates the space coordinates that have been determined (or at least the X component thereof) of the reference position at the point in time of the determination of the actual value.

A setpoint value is compared with a corresponding actual value—or two actual values are compared with one another—and the deviation is determined. Apart from the negligible thermal expansion, the absolute location of the reference position(s) within the pharmacy order-picking system. In the ideal case (which corresponds to the original condition, for example, in which the setpoint values were determined), the actual value is identical to the setpoint value. However, if a deviation is found, this means that a different number of motor steps would be needed for reaching/approaching the reference position(s) in X direction (when using a stepping motor, for example). The positioning is no longer accurate if the control unit is running a control program that presupposes faultless, e.g., undisturbed drive mechanism(s). X motor steps may be taken until reaching a certain reference position if the drive mechanism is not disturbed. However, if the drive mechanism is disturbed, $X+\Delta X$ or $X-\Delta X$ motor steps may be taken until reaching the reference point. Therefore, if one does not have knowledge of the disturbance, the wrong position is approached by $\Delta X$ steps.

If two actual values are compared with one another, then a deviation indicates that a number of motor steps different from what is expected (when using a stepping motor, for example) would be necessary for traveling the distance between the two reference points in X direction. This deviation also indicates that positioning based on the control program present in the control unit is no longer precise.

If a deviation exceeding the limit value is detected, then a signal indicating the need for a correction is output.

A method described herein reduces the need for manual retrieval of a drug package and reduces the susceptibility of the system in that checks are performed at predefined intervals to ascertain whether the positioning in X direction is still precise enough. If this is not the case, then a corresponding signal is output, and this signal may vary, depending on the type and size of the deviation, for example. When there are only minor deviations, an internal adjustment can be made to ensure continuation of automatic operation.

With a pharmacy order-picking system, the X-direction/X-axis is usually the direction in which the operating unit moves horizontally. Depending on how the drug packages are placed on the shelf, the X axis is usually also the longest axis, which has the resulting effect that the operating unit is often moved particularly frequently along this axis and deviations in the positioning accuracy can have especially strong effects.

In a preferred embodiment of a method described herein, in addition to detecting a position deviation in the horizontal direction (X axis) the Z axis (vertical axis) is also investigated with regard to a position deviation.

To do so, at least one setpoint value of at least one reference position is made available. This may be, for example, the location of one or more shelves. With the operating unit, a position corresponding to the setpoint value is approached, and with the sensor turned on, the gripping device is moved further to the setpoint value and on detecting a signal that is characteristic of the reference position, the actual value of this reference position is determined. A setpoint value is then compared with a corresponding actual value or two actual values are compared with one another and the deviation if any is determined. If a deviation exceeding a limit value is ascertained, then a signal indicating the need for a correction is output, and this signal may vary with the type and size of the deviation.

Due to the enormous variety of pharmaceutical drugs, i a large variety of different drug packages may be on hand. Therefore, a large storage area within the pharmacy order-picking system may be desired. This may be achieved by widening the device in the X and/or Z directions, for example. Another possibility is to install two shelving areas, usually in parallel. Each shelf unit may be assigned its own operating unit, but in view of the cost-intensive components of the operating unit, it is preferable to install only one operating unit. To be able to operate both shelf units, it is necessary for the gripping device of the operating unit to be rotatable by at least 180° (C axis), so that both shelf units can be operated from the front for placing items on the shelf and retrieving them from the shelf. Even if the gripping device can rotate about the C axis, there may be deviations in positioning, for example, such that the device is rotated not by 180° but instead by 180°+X° or 180°−X° (for example, due to slippage of the rotary motor when the rotation is too low).

Therefore, in a preferred embodiment of a method described herein, the rotation about the C axis is also tested. The pharmacy order-picking system, which is operated with the preferred embodiment of a method described herein, includes at least two parallel shelf units between which the operating unit can be moved horizontally and vertically, such that the gripping device of the operating unit can be rotated and/or pivoted about the vertical axis.

For detecting a positioning deviation in the gripping device with respect to the C axis of rotation, first a check is performed, as already described above, with respect to the positioning deviation in the X direction in relation to one of the shelf units. The gripping device is then rotated by a predefined value C such that this value in the ideal case (without interference in the rotation about the C axis of rotation) induces a rotation by 180°.

A check is performed as to whether there is a deviation in positioning in the X direction in the second shelf unit. Therefore, a second position corresponding to a second setpoint value is approached by the operating unit for the second shelf unit (thus at least one reference position in X direction is supplied per shelf unit). With the sensor turned on, the gripping device is advanced further to the setpoint value, and when a signal that is characteristic of the second reference position is detected, the actual value of the reference position is ascertained. The setpoint value of the second reference position is compared with the actual value, and the deviation, if any, is determined. If the deviations thereby ascertained with respect to the first and second shelf units exceed the limit values or if they differ by a predefined value, a signal is output indicating the need for a correction, such that the signal varies as a function of the deviations thereby ascertained.

Deviations in the position accuracy with regard to the C axis are thus not ascertained directly thereon but instead are ascertained indirectly based on positioning deviations with respect to the X axis of the shelf units.

The operating unit can usually be moved in both horizontal and vertical directions with the help of guide rails. Depending on the design of the pharmacy order-picking system, two horizontal guide rails are used, such that the vertical guide rail is guided horizontally with the gripping device on these guide rails. Each guide rail may be assigned an independent drive mechanism (or one section of a central drive mechanism), and the drive mechanisms ensure movement (preferably in synchronization) along the horizontal guide rails.

If the drive mechanisms do not move in synchronization on the vertical guide rail, this may lead to an inclined position of the vertical guide rail, and such an inclined position will in turn influence the positioning accuracy of the operating unit and of the gripping device.

In a preferred embodiment of a method described herein, a setpoint value of at least one reference position is made available; with this setpoint value, the operating unit approaches a position corresponding to the setpoint values for detecting an inclined position of the operating unit for the upper and lower guide rails; on detection of a signal that is characteristic of a reference position, one actual value is ascertained per reference position, and the setpoint values are compared with the actual values, one deviation being ascertained for each reference position. Finally, if the deviations thereby ascertained differ by more than a predefined limit value, a signal indicating the need for a correction is output, such that this signal depends on the size of the differential value.

In a preferred embodiment of a method described herein, a service query is transmitted electronically to a service employee and/or the pharmacy order-picking system is shut down, depending on the signal indicating the need for a correction. A service query may be transmitted when the deviations/differences detected exceed the predefined limit values, but a malfunction of the system can be largely ruled out. Maintenance of the system may be initiated in this way before it is necessary to shut down the system and necessary for the user to intervene.

The setpoint value(s) may be made available by saving the setpoint value(s) as predefined values in the control unit. This procedure is extremely simple and can be implemented quickly but may utilize a very high measure of manufacturing precision. It is preferable for the setpoint value(s) of at least one reference position to be made available by the fact that the setpoint value(s) is/are learned. For example, after the initial startup of operation of the pharmacy order-picking system in that predefined reference positions are approached and, on detection of a signal that is characteristic of a certain reference position, a value is ascertained, this value being saved as the setpoint value in the control unit.

In the case of large-scale pharmacies in particular, the pharmacy order-picking system is more or less in continuous operation, so that it is desirable for a method described herein to be implementable as rapidly as possible. Therefore, in a preferred embodiment of a method described herein, a position corresponding to a setpoint value is approached at a first speed v1 and the operating unit is moved further in the direction of the reference position at a second speed v2 until a signal that is characteristic of the reference position is detected, such that speed v2 is less than speed v1.

The operating unit may be driven at full speed, for example, to the position corresponding to the setpoint value. If the sensor is not operating continuously, the sensor can be turned on. The operating unit is moved further at a reduced speed until a signal that is characteristic of the reference position is detected. The reduced speed contributes toward an increase in measurement accuracy, and the combination with a distance traveled at full speed permits a rapid and at the same time reliable implementation of the method.

The deviations in positioning may be caused by a variety of factors, which are described in further detail below, so that it is not necessarily possible to conclude the cause from the deviations ascertained. However, to the extent that it is definite and the basis of the deviations ascertained, causing the deviation in positioning, in a preferred embodiment of a method described herein, one or more corresponding correction factors are ascertained is/are ascertained on the basis of the deviation(s) detected, these correction factors are stored in the control unit and control programs executed subsequently take this/these correction factor(s) into account in controlling the operating unit.

BRIEF DESCRIPTION OF THE DRAWINGS

A method described herein is described in greater detail below on the basis of preferred embodiments that are shown only schematically in the drawings, in which:

FIGS. 4a-4c illustrate sectional views of a section of a pharmacy order-picking system, wherein the figures are to be used to illustrate a method described herein.

FIG. 5a-5b illustrate sectional views of one section of a pharmacy order-picking system, wherein the figures are supposed to illustrate a method described herein.

FIG. 6 illustrates a schematic view of one section of a pharmacy order-picking system wherein the figure should serve to illustrate a method described herein.

DETAILED DESCRIPTION

Figure 1:
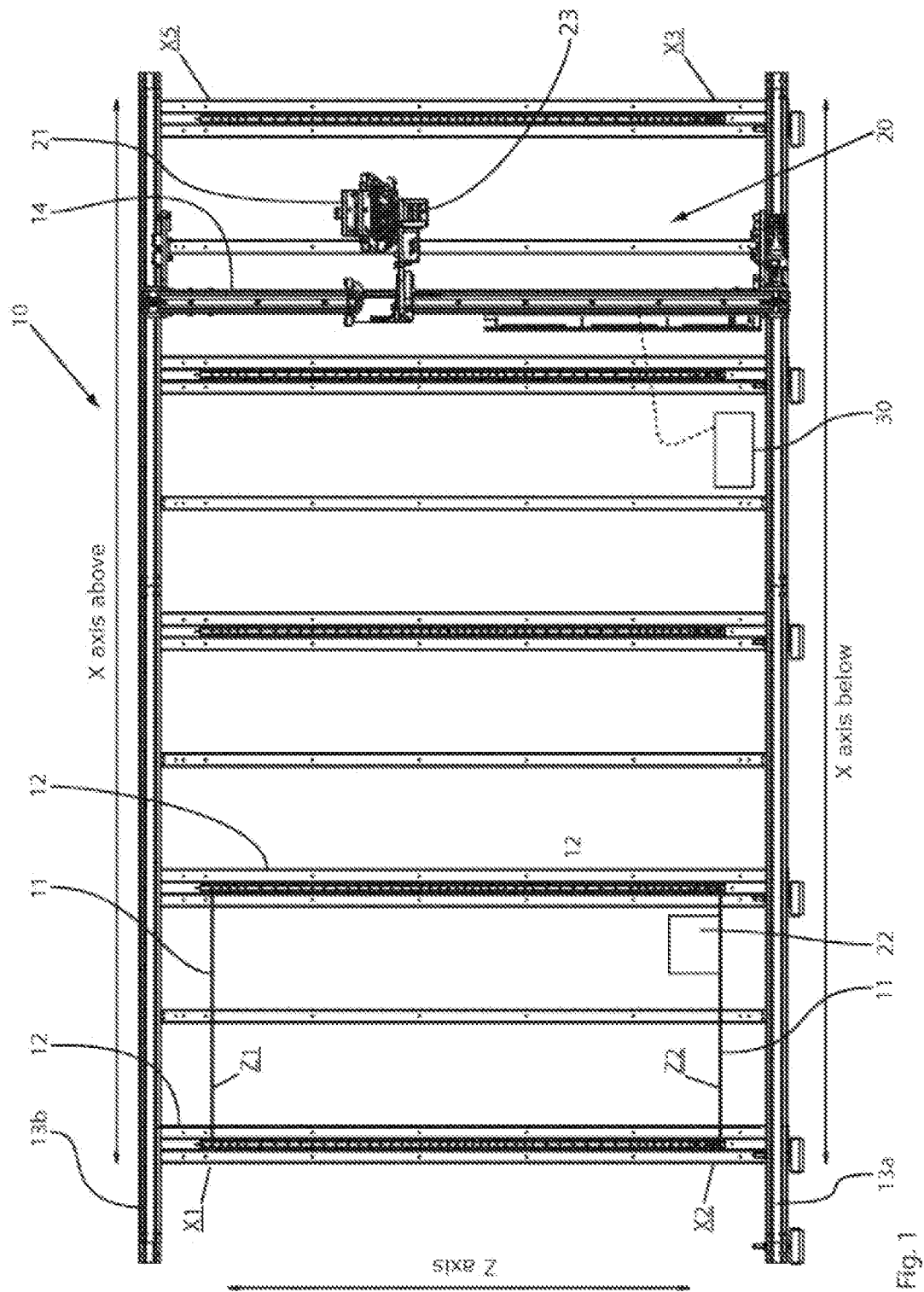
FIG. 1 illustrates a lateral sectional view of a shelf unit of a pharmacy order-picking system.

FIG. 1 illustrates a lateral sectional view of a pharmacy order-picking system having two shelf units, but only one shelf unit 10 is shown here. The pharmacy order-picking system also includes an operating unit 20 that can be moved horizontally and vertically between the shelf units 10. The shelf units each comprise a plurality of shelves 11 extending in the horizontal direction (X axis) and a plurality of shelf walls 12 extending in the vertical direction (Z axis). The shelves 11 are usually made completely of glass with a smooth surface. Drug packages 22 are stored in a chaotic fashion on the shelves 11 with optimal utilization of space.

The operating unit 20 can be moved horizontally and vertically between shelf units 10 with the help of two horizontal guide rails (13a, 13b) and one vertical guide rail (14) and the drive units assigned to them. The vertical guide rail 14 is movably attached to the horizontal guide rails 13a, 13b for this purpose. The operating unit 20 includes a gripping device 21, which can be moved vertically on the guide rail 14 by means of a corresponding drive mechanism as well as a gripper jaw and/or a vacuum gripper. The gripping device 21 also includes a sensor 23 with which the distance from the sensor to the back wall (see FIG. 2) of the shelf unit, stored drug packages 22 or components of a shelf unit (shelf walls, shelves), can be determined.

The sensor 23 may be, for example, an optical sensor according to the triangulation method which determines the distance from the plane spanned by the two horizontal guides at a 90° angle (ideal value, positioning deviations possible; see FIGS. 5a, 5b in this regard). In another embodiment, an inductive proximity sensor may be used, with metallic reference points to be used in this case.

The operating unit 20 is electronically connected to a control unit 30, which is shown only schematically here. The control unit 30 may comprise a plurality of computers (not shown) and controls the entire operation of the system (identification, placement on a shelf and retrieval from the shelf, etc.).

With the pharmacy order-picking system shown in FIG. 1, seven reference positions (X1, X2, X3, X4, X5, Z1, Z2) are provided (reference position X4 is situated on the shelf unit, which is not shown and therefore is not "visible" in FIG. 1). However, this number of reference positions may be necessary when all of the positioning deviations described below are to be ascertained—in other embodiments, it may be adequate to have only one reference position.

Reference positions may be provided by any points that can be detected by the sensor within the pharmacy order-picking system. In the following description of the method, it is assumed that the reference positions are provided by shelves (positions Z1, Z2) and walls (positions X1, X2, X3, X4, X5). The reference positions in this case are therefore not additional structural measures. In other embodiments the reference positions may also be provided by specific components (signal generators, etc.).

Figure 2:
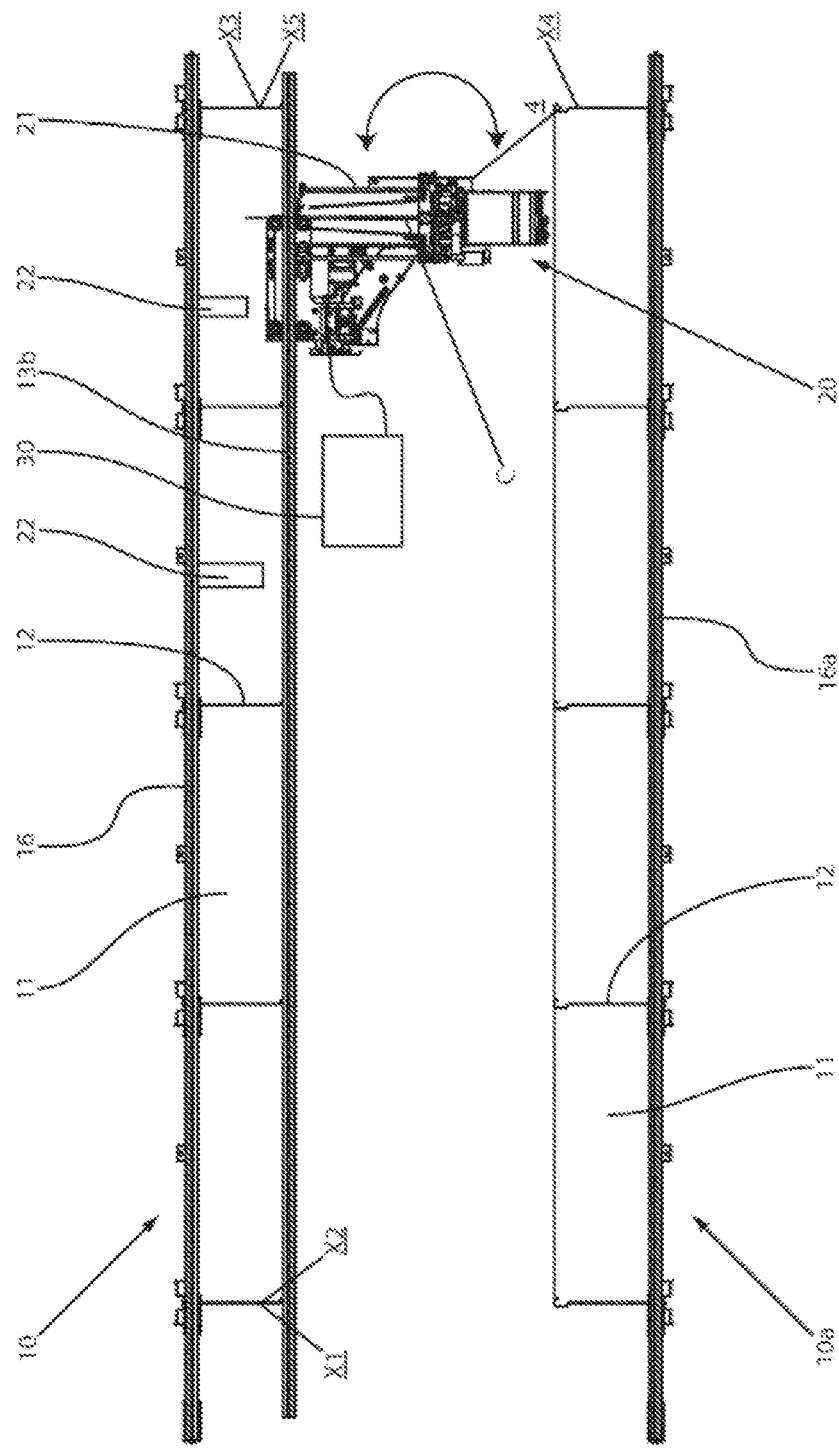
FIG. 2 illustrates a top view of a pharmacy order-picking system.

FIG. 2 illustrates a top view of a section of a pharmacy order-picking system wherein the two parallel shelf units 10, 10a are visible in this figure, with the operating unit 20 being movable horizontally and vertically between them with the help of the guide rails 13a, 13b, 14. For placing drug packages on the shelf or retrieving them from the shelf, the gripping device 21 of the operating unit 20 is aligned at a 90° angle to the back wall 16, 16a of the corresponding shelf unit 10, 10a. The operating unit 20 is itself high-maintenance and cost-intensive, so it is customary to install just one operating unit for two parallel shelf units in a pharmacy order-picking system. To be able to operate the two shelf units, the gripping device can be rotated about an axis of rotation C, as indicated in FIG. 2. The reference position X4, which is not "visible" in FIG. 1, is provided by a component of the shelf unit 10a (shelf wall 12).

Figure 3:
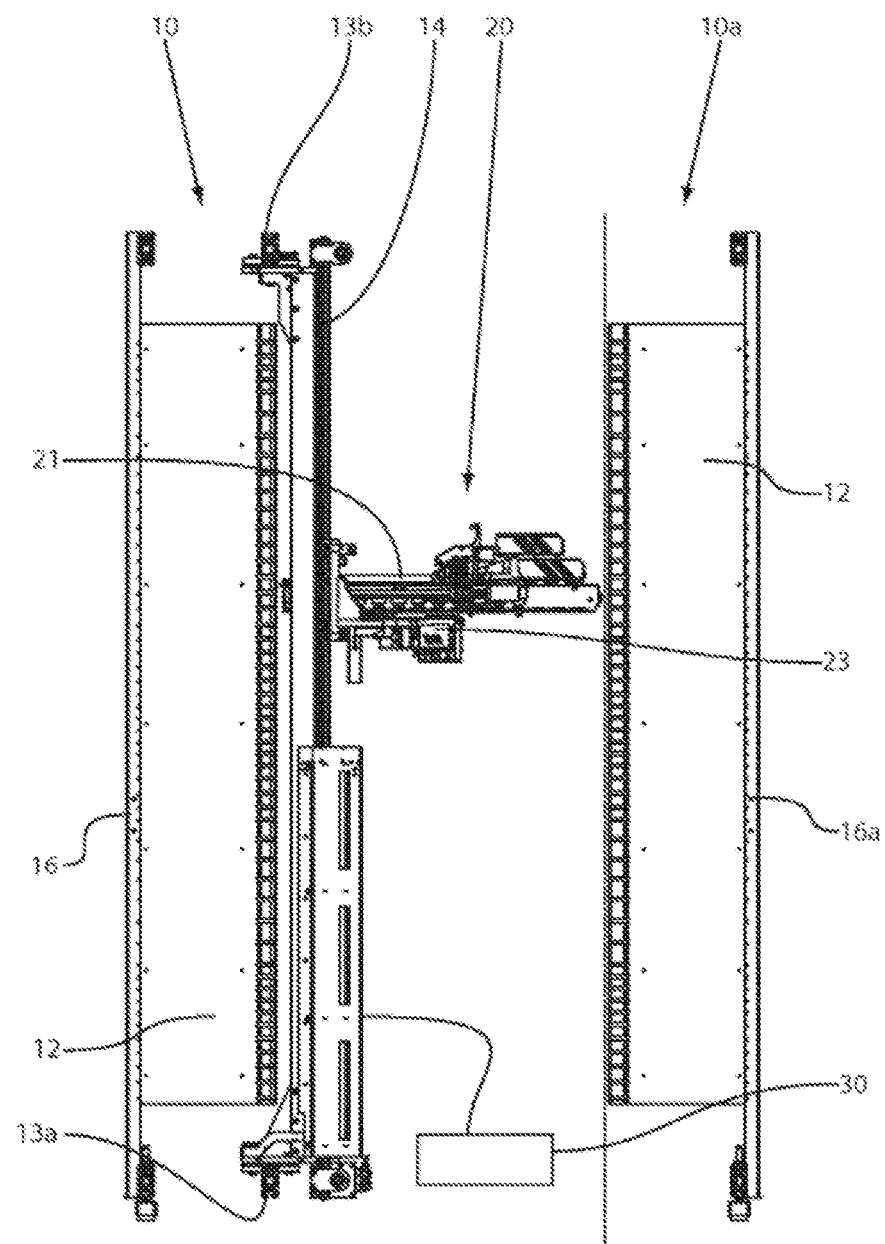
FIG. 3 illustrates a sectional view of a pharmacy order-picking system.

FIG. 3 illustrates a sectional view of the pharmacy order-picking system. The operating unit 20 can be moved horizontally and vertically on guide rails 13a, 13b between the two shelf units 10, 10a. Those skilled in the art are familiar with details of how the operating unit can be moved on the guide rails, so these details are not essential to the present disclosure. The vertical guide rail 14 is usually moved on the horizontal guide rails 13a, 13b with the help of one or two toothed belts and one or more drives. Likewise, the gripping device 21 together with the sensor 23 is usually moved vertically on the vertical guide rail 14 with the help of a toothed belt and a corresponding drive.

With reference to FIGS. 4a-4c, 5a-5b and 6, embodiments of a method described herein are described below. The diagrams of sections of a pharmacy order-picking system selected to illustrate a method described herein are highly schematic, in order not to obscure the nature of a method described herein due to unnecessary structural details.

X-Axis Positioning Deviation

With reference to FIGS. 4a-4c, one embodiment of a method described herein is described below, this embodiment regarding positioning deviations with regard to the X axis.

A positioning deviation with respect to the X axis can be detected in general on the basis of one reference point (based on a benchmark). However, no conclusion can be drawn about the type of deviation on the basis of this one deviation detected (elongation in length of toothed belts, mechanical slippage, etc.). Therefore, an embodiment of a method described herein, in which two reference points (X2, X3) for ascertaining a positioning deviation are verified, is described below.

FIGS. 4a-4c illustrate a schematic sectional view of one section of a pharmacy order-picking system having two shelf units 10, 10a and one operating unit that can be moved horizontally and vertically between the shelf units; only the gripping device 21 is indicated schematically for the sake of simplicity. The view according to the aforementioned figures shows the lower portion of the pharmacy order-picking system, and therefore only the reference positions X2, X3 and X4 are indicated.

The numerical data given in the figures refer to the X component of the space coordinates of various reference positions, where only the numbers that are intended to illustrate the method as such.

In a method described herein for operating a pharmacy order-picking system, two setpoint values $X_{2S}$, $X_{3S}$ for the reference positions X2, X3 of shelf unit 10a are provided for detecting a position deviation of the operating unit in the horizontal direction (X axis). The setpoint values of the aforementioned reference positions are each embodied in FIGS. 4a-4c in the unit labeled as "setpoint" at the left ($X_{2S}$=10, $X_{3S}$=45).

As mentioned above, the setpoint values mentioned above can be provided by storing them only in the memory of the control unit or by having them learned at the time of (initial) start of operation of the pharmacy order-picking system. In the (initial) start of operation, the operating unit is therefore moved from a reference position, the position of which is predetermined (e.g., the "zero point" of the operating unit) at a first speed (preferably the maximum speed of the operating unit in the X direction) to a preliminary position $X_{2V}$ which corresponds to the first setpoint value $X_{2S}$. Beyond this preliminary position $X_{2V}$, the operating unit with the sensor turned on is moved further in the direction of the reference position X2. As soon as the reference position has been reached, the sensor detects a characteristic signal. In the exemplary embodiment shown here, the reference position X2 is provided by a shelf wall, and the sensor detects a characteristic signal (change in flank in the digital output signal or change in level with an analog output signal). The space coordinates (or at least the X component thereof) is saved as the setpoint value $X_{2S}$ for the reference position X2. Accordingly, the movement is performed using the reference position X3, and it is not necessary to return the operating unit to the reference point. According to FIG. 4a, the reference positions X2 and X3 are approached from the left. However, that is not necessary. In the method, it is irrelevant from which side the reference positions are approached with the sensor turned on.

After providing the setpoint values for the reference positions X2, X3, the operating unit 20 approaches a position corresponding to the setpoint value $X_{2S}$ in the horizontal direction. The aforementioned position $X_{2V}$ is situated at X coordinate 5. With the sensor turned on, the operating unit is now moved further toward the setpoint value and on detecting a signal that is characteristic of the reference position X2, an actual value $X_{2I}$ is ascertained for the reference position X2. As soon as the actual value for the reference position has been ascertained, the operating unit is moved to a position $X_{3V}$ corresponding to the setpoint value X3 and the operating unit 20 is moved further in the direction of the reference position X3 starting from this position, and on detecting a signal that is characteristic of the reference position X3, an actual value $X_{3I}$ for this reference position is ascertained.

The actual values $X_{2I}$, $X_{3I}$ thereby ascertained are compared with the corresponding setpoint values $X_{2S}$, $X_{3S}$ and one deviation is ascertained per reference position X2 and X3 ($A_{X2}$, $A_{X3}$). A deviation may also be determined by subtracting the two actual values thereby ascertained for the reference positions X2, X3 from one another (e.g., the distance between the actual values $X_{2I}$, $X_{3I}$ is ascertained) and the value thereby ascertain is compared with the difference in the corresponding setpoint values.

If a deviation $A_{X2}$, $A_{X3}$, $A_{X23}$ which exceeds the limit value is ascertained, a signal indicating the need for a correction is output. For example, it may be displayed to the user that a positioning deviation with respect to the X axis has been ascertained and the service has been informed accordingly. If the deviations thereby ascertained no longer allow reliable operation of the system, the system is stopped and the service is informed.

The deviations thereby ascertained allow inferences regarding the type of disturbance in the positioning accuracy. In the case illustrated in FIG. 4a, the actual values for the reference positions X2, X3 correspond to the setpoint values. It follows from this that there is not any disturbance in the positioning accuracy with regard to the X axis. In the case illustrated in FIG. 4b, a deviation $A_{X2}$=1 is ascertained with respect to the reference position X2, and a deviation $A_{X3}$=5 is ascertained with regard to the reference position X3, from which it is possible to conclude that there has been an elongation in the length of the tooth belt(s) of the drive mechanism for the X axis. On the basis of the deviations thereby ascertained, a correction factor which can be used in the further positioning of the operating unit may be ascertained.

In the case illustrated in FIG. 4c, a deviation $A_{X2}$, $A_{X3}$=2 is ascertained for each of the two reference positions X2, X3. It follows from this that there is no elongation in the length of the toothed belt(s) of the drive mechanism for the movement of the operating unit in the X direction, but there is an offset which indicates a mechanical slippage or a jumping of the tooth belt over a corresponding drive gear.

C Axis Positioning Deviation (Axis of Rotation of the Gripping Device and the Operating Unit)

With reference to FIGS. 4a, 5a, 5b, one embodiment of a method described herein is described below in which the positioning accuracy with regard to the C axis (axis of rotation of the gripping device of the operating unit) is ascertained.

In this embodiment of a method described herein, first the setpoint values for the reference positions X3, X4 are provided as described above. Next the positioning deviation with regard to the reference X3 is ascertained in the manner already described with reference to the X axis. A position deviation with regard to the X axis is then ascertained at a reference position X4 of the other shelf unit 10.

To do so, the grouping device 21 of the operating unit is rotated by a predetermined value C with this rotation by the predetermined value C corresponds to a rotation by 180° in the ideal case. Then a second position $X_{4V}$ corresponding to a second setpoint value $X_{4S}$ is approached with the operating unit. In the schematic diagrams shown in FIGS. 4a, 5a-5b, this position $X_{4V}$ is at the right of the reference X4. With the sensor turned on, the operating unit is then moved further in the direction of the reference position X4, and an actual value $X_{4I}$ of the reference position is ascertained on detecting a signal that is characteristic of the reference position X4. Next, the setpoint value of the second reference position X4 is compared with the actual value and a deviation $A_{X4}$ is determined. If the deviations ascertained for the reference positions X3 and X4 exceed limit values or if they are different by a predefined value, then a signal indicating the need for a correction is output.

The type of positioning deviation can be deduced from the ascertained deviations $A_{X3}$, $A_{X4}$. In the case illustrated in FIG. 4a, the deviations for the reference positions X3 and X4 are both the same (they are both 0), which means that there is no positioning deviation with respect to the C axis of rotation (if other positioning deviations with respect to the X axis can be ruled out).

FIG. 5a illustrates a case in which the gripping device 21 is not oriented at a 90° angle to the shelf unit 10a but instead the angle to the shelf unit is adjusted slightly clockwise. In determining the actual value for the reference position X3, therefore this is not detected at X=45 (as would be the case with a 90° angle), but instead is detected only at X=46. After rotation at the gripping device 21 by a value C (corresponding to the ideal angle of 180° in this case), the actual value for the reference position X4 is determined. Based on the faulty positioning of the gripping device with respect to the shelf unit 10, the actual value of the reference position at x=44 is determined. A comparison at the setpoint values with the actual values for the reference positions X3, X4 shows that the deviations are the same ($A_{X3}$, $A_{X4}$) and are greater than 0, which indicates a false position of the gripping device 21 with respect to the shelf walls.

FIG. 5*b* illustrates a case in which the rotation by the amount C is not rotation by 180° but instead is by a reduced angle. With regard to the reference position X3, a deviation of $A_{X3}=0$ is determined and for the reference position X4, a deviation of $A_{X4}=1$ is determined. If faultless positioning with regard to the X axis is assumed, this means that the rotation by the value C does not result in rotation by 180°, so that positioning accuracy with regard to the C axis is disturbed.

Z-Axis Positioning Deviation

Referring to FIG. 6, one embodiment of a method described herein will now be described briefly. In this embodiment a positioning deviation with regard to the Z axis is also determined.

A positioning deviation with regard to the Z axis can be determined in general according to the positioning deviation with regard to the X axis. That is, either a positioning deviation starting from a reference point is determined with respect to the reference positions Z1, Z2 or a difference in the actual values of the reference points Z1, Z2 is determined and this is compared with the difference between the setpoint values of the reference points Z1 and/or Z2. If a deviation between the difference in the setpoint values and actual values is detected, one can conclude from this that there has been an increase in the length of a tooth belt that has been used, if any, for positioning the gripping device 21. The details regarding the performance of the method for determining a positioning deviation in the Z axis are comparable with those of the method for determining a positioning deviation with regard to the X axis, so that a renewed detailed presentation will not be given here.

To determine whether there is an inclined position of the vertical guide rail, positioning deviations in two reference positions with different Z axis positions are determined. In the present case, a possible inclined position of the Z axis can be determined, in which positioning deviations with regard to the X axis are determined for the reference positions X1, X2 or X3, X5. In the determining of a possible inclined position of the Z axis, the two measured reference positions should be situated on a shelf unit to rule out possible influences due to a positioning deviation with regard to the C axis of rotation of the gripping device. The possible positioning deviations with regard to the two reference positions are compared and in the event of a deviation in these from one another, an inclined position of the Z axis (vertical guide rail) can be concluded and when a limit value is exceeded, a signal indicating the need for a correction is output.

The invention claimed is:

1. A method for operating a pharmacy order-picking system, the method comprising:
   providing the pharmacy order-picking system comprising:
      at least two parallel shelf units, each having a plurality of shelves extending in a horizontal direction and a plurality of shelf walls extending in a vertical direction,
      at least one operating unit that can be moved horizontally and vertically in front of one of the two parallel shelf units, having a gripping device for placing drug packages on the shelves and retrieving the drug packages from the shelves, wherein the operating unit is configured to rotate by at least 180° about the vertical direction for the gripping device to reach each of the two parallel shelf units, the operating unit comprising:
         at least one sensor, and
         a control unit that is connected to the operating unit,
      detecting a positioning deviation of the operating unit in the horizontal direction, the detecting comprising:
         a) providing, for at least one reference position, a setpoint value,
         b) approaching, with the operating unit, in the horizontal direction, the at least one reference position,
         c) determining, on detection of a signal that is characteristic of the reference position, an actual value of the reference position,
         d) comparing the setpoint value with a corresponding actual value or comparing two actual values with one another and determining a horizontal deviation, and
         e) when the horizontal deviation exceeds a limit value, outputting a signal indicating a need for a correction, and
      detecting a positioning deviation of the gripping device with respect to a vertical axis of rotation based on the positioning deviation of the operating unit in the horizontal direction, and
      rotating the gripping device by a predefined value based on the detected positioning deviation of the gripping device.

2. The method of claim 1, further comprising detecting a positioning deviation of the operating unit in a vertical direction, the detecting comprising:
   a) providing, for a vertical reference position, a vertical setpoint value,
   b) approaching, with the operating unit, vertical reference position,
   c) determining, on detection of a signal that is characteristic of the vertical reference position, an actual value of the vertical reference position,
   d) comparing the setpoint value with the corresponding actual value or comparing two actual values with one another, and determining a vertical deviation and
   e) when the vertical deviation exceeds a limit value, outputting a signal indicating the need for a correction.

3. The method of claim 1, further comprising:
   approaching, in the horizontal direction, a second reference position corresponding to a second setpoint value with the operating unit,
   ascertaining, on detection of a second signal that is characteristic of the second reference position, an actual value of the second reference position,
   comparing the setpoint value of the second reference position with the actual value and determining a second horizontal deviation, and
   when the horizontal deviation and the second horizontal deviation exceed limit values, or when the horizontal deviation and the second horizontal deviation differ by a predefined value, outputting a signal indicating the need for a correction.

4. The method of claim 1, wherein the pharmacy order-picking system further comprises two horizontal guide rails and one vertical guide rail, wherein the vertical guide rails can be moved along the horizontal guide rails and the gripping device can be moved along the vertical guide rail, and wherein the method further comprises:
   detecting an inclined position of the operating unit, wherein the detecting comprises:

a) providing at least one setpoint value of at least one reference position for an upper guide rail and at least one setpoint value of at least one reference position for a lower guide rail,
b) approaching the at least one reference position for the upper guide rail, and approaching the at least one reference position for the lower guide rail, with the operating unit,
c) determining, on detecting a signal that is characteristic of the reference position for the upper guide rail, an actual value of the reference position of the upper guide rail and ascertaining, on detecting a signal that is characteristic of the reference position for the lower guide rail, an actual value of the reference position for the lower guide rail,
d) comparing the setpoint value for the upper guide rail with the actual value for the upper guide rail, and determining an upper guide rail deviation and comparing the setpoint value for the lower guide rail with the actual value for the lower guide rail, and determining a lower guide rail deviation, and
e) when the upper guide rail and lower guide rail deviations differ by a predefined value, outputting a signal indicating the need for a correction.

5. The method of claim 1, further comprising, on the signal indicating the need for the correction, transmitting a service query electronically to a service employee, and shutting down the pharmacy order-picking system.

6. The method of claim 1, wherein providing the setpoint value of the at least one reference position comprises storing the setpoint value as predefined values in the control unit.

7. The method of claim 1, wherein providing the setpoint value of the reference position comprises learning after a first startup of operation of the pharmacy order-picking system by approaching predefined reference positions and, on detecting a signal that is characteristic of a certain reference position, ascertaining a value and ascertaining a setpoint value and storing the value in the control unit.

8. The method of claim 1, wherein the reference position corresponding to the setpoint value is approached at a first speed, and the operating unit is moved further in a direction of the reference position at a second speed until a signal that is characteristic of the reference position is detected.

9. The method of claim 1, ascertaining one or more corresponding correction factors based on an ascertained horizontal deviation, storing the corresponding correction factors in the control unit and taking into account the corresponding correction factors when a control programs control the operating unit.

* * * * *